US00PP32187P3

(12) United States Plant Patent
Bell et al.

(10) Patent No.: US PP32,187 P3
(45) Date of Patent: Sep. 15, 2020

(54) BLUEBERRY PLANT NAMED 'MG11654-24-001'

(50) Latin Name: ***Vaccinium* hybrid**
Varietal Denomination: MG11654-24-001

(71) Applicant: Moondarra Genetics Pty Ltd, Moondarra, Victoria (AU)

(72) Inventors: Ridley Bell, Lindendale (AU); Joel Deveson, Newborough (AU)

(73) Assignee: Moondarra Genetics PTY LTD, Moondarra (AU)

( * ) Notice: Subject to any disclaimer, the term of this patent is extended or adjusted under 35 U.S.C. 154(b) by 0 days.

(21) Appl. No.: 16/501,664

(22) Filed: May 20, 2019

(65) Prior Publication Data

US 2019/0373786 P1 Dec. 5, 2019

Related U.S. Application Data

(60) Provisional application No. 62/762,828, filed on May 22, 2018.

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 6/368; A01H 5/08
See application file for complete search history.

*Primary Examiner* — Keith O. Robinson
(74) *Attorney, Agent, or Firm* — Plant & Planet Law Firm

(57) ABSTRACT

The new blueberry plant variety 'MG11654-24-001' is provided. 'MG11654-24-001' is a commercial variety intended for the fresh fruit market. The variety is produced from a cross of 'Duke' (seed parent, not patented) and 'Ridley 1403' (pollen parent, U.S. Plant Pat. No. 25,432), which can be distinguished by its outstanding features.

3 Drawing Sheets

Latin name of the genus and species:
Genus—*Vaccinium.*
Species—hybrid.

VARIETY DENOMINATION

The new blueberry plant claimed is of the variety denominated 'MG11654-24-001'.

BACKGROUND OF THE INVENTION

The proposed new variety 'MG11654-24-001' was selected as a seedling from a controlled pollination involving northern and southern highbush varieties 'Duke' (seed parent) (not patented) and 'Ridley 1403' (pollen parent) (U.S. Plant Pat. No. 25,432) respectively. The cross was made in 2011 in Moondarra, Victoria, Australia and the variety was selected in 2014 in Moondarra, Victoria, Australia. This new cultivar has been asexually propagated through cuttings since 2016 and grown in replicated field trials from 2017 in Moondarra, Victoria, Australia. The plants of 'MG11654-24-001' are tough and vigorous with an upright to whippy growth habit while the fruit is very crunchy, large and firm with a good flavor and bloom.

SUMMARY OF THE INVENTION

As mentioned above, the proposed new cultivar 'MG11654-24-001' is a result of a cross between 'Duke' and 'Ridley 1403', whose characteristics are discussed below.

The seed parent 'Duke' is a northern highbush variety with early fruit ripening, high chill requirement and high yields with medium to large fruit and a moderate to strong bloom.

The pollen parent 'Ridley 1403' was produced from a southern highbush seedling selection of 'S02-25-05' (unpatented) and pollen parent 'S03-08-02' (unpatented) and was selected in 2008 at Lindendale, New South Wales, Australia with the criteria of strong plant vigor, early-mid fruit ripening, very large fruit size and very firm/crunchy fruit texture.

The proposed new variety 'MG11654-24-001' is a selection from seedlings produced from a controlled pollination between 'Duke' and 'Ridley 1403' in the breeding program at Moondarra, Victoria, Australia in 2011.

Asexual reproduction of the proposed new variety 'MG11654-24-001' by cutting propagation has occurred since 2016 at Moondarra, Victoria, Australia. This has demonstrated that the new variety is uniform, stable and true to type over successive generations of asexual propagation in respect to the characteristics aforementioned.

The proposed new cultivar 'MG11654-24-001' was selected as a single plant in a population of seedlings resulting from a cross between 'Duke' and 'Ridley 1403' and selected in 2014 at Moondarra, Victoria, Australia. The selection of 'MG11654-24-001'; was based upon the characteristics of strong plant vigor and bush toughness, early fruit ripening and large, firm, crunchy berries with a good flavor and bloom. 'MG11654-24-001' has been evaluated in field trials since 2017 at Moondarra, Victoria, Australia.

The following characteristics of the proposed new variety have been observed and used to distinguish 'MG11654-24-001' as a distinct cultivar of *Vaccinium* hybrid:

Very early-season fruit ripening.
Strong plant vigor.
Upright/whippy growth habit.

Large berry size.
Crunchy berry texture.
Small dry picking scar.
Sweet berry flavor.
Good light colored bloom.

The proposed new variety 'MG11654-24-001' differs from the seed parent 'Duke' as previously described in terms of 'MG11654-24-001' possessing a possible lower chill requirement, very early fruit ripening, large fruit and a crunchy fruit texture.

'MG11654-24-001' differs from pollen parent 'Ridley 1403' in respect to having an expected higher chill requirement, smaller berry size and reduced plant vigor.

The proposed new variety 'MG11654-24-001' is uniform, stable and true to type over successive generations of asexual propagation through softwood cuttings in respect to the characteristics aforementioned.

BRIEF DESCRIPTION OF THE DRAWINGS

The accompanying photographic illustration shows typical specimens in full color of the foliage and fruit of the new variety 'MG11654-24-001' 'MG11654-24-001' has been labeled Merliah NB-24-1 in the photographs. The colors are as nearly true as is reasonably possible in a color representation of this type.

Figure 1:
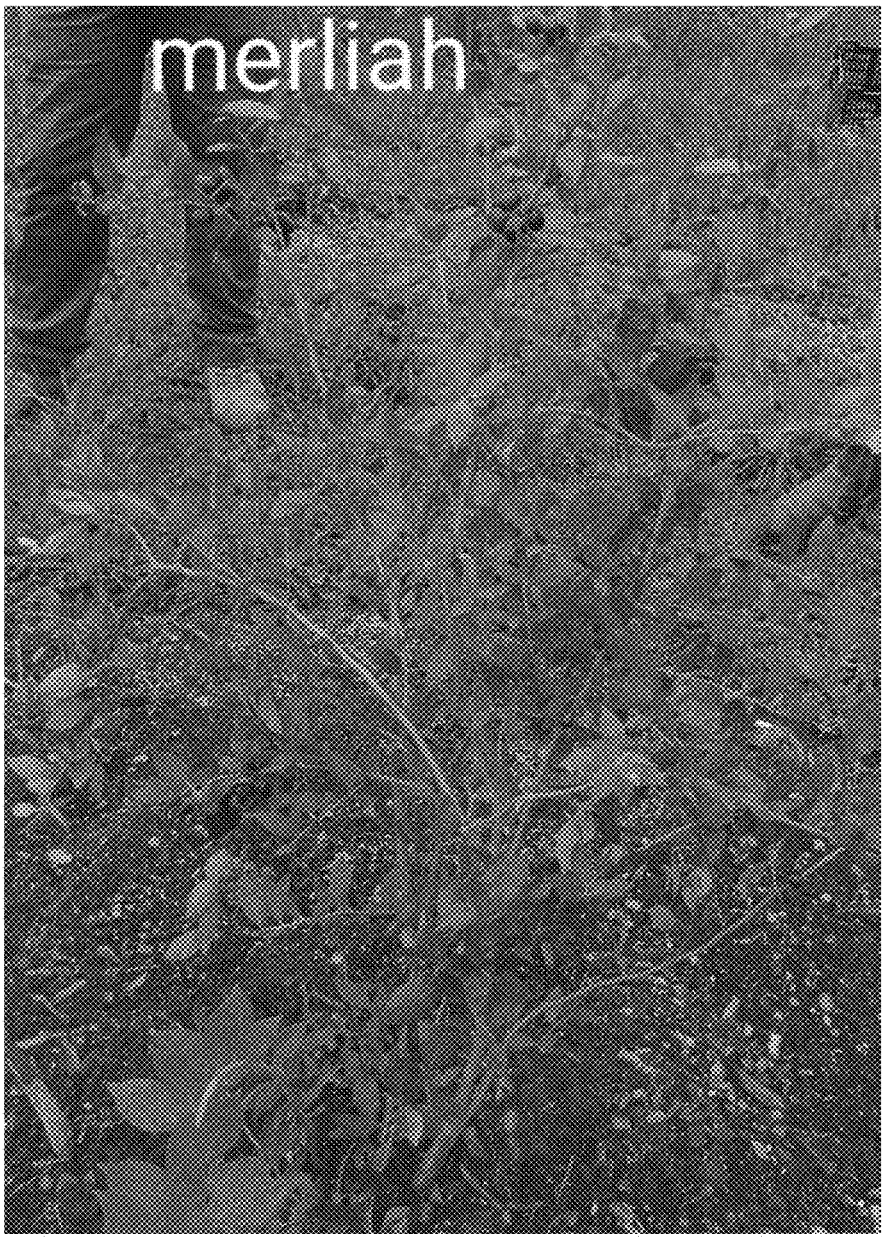
FIG. 1 is a photograph of the fruit of the new variety 'MG11654-24-001' at approximately 1 year of age.
Figure 2:
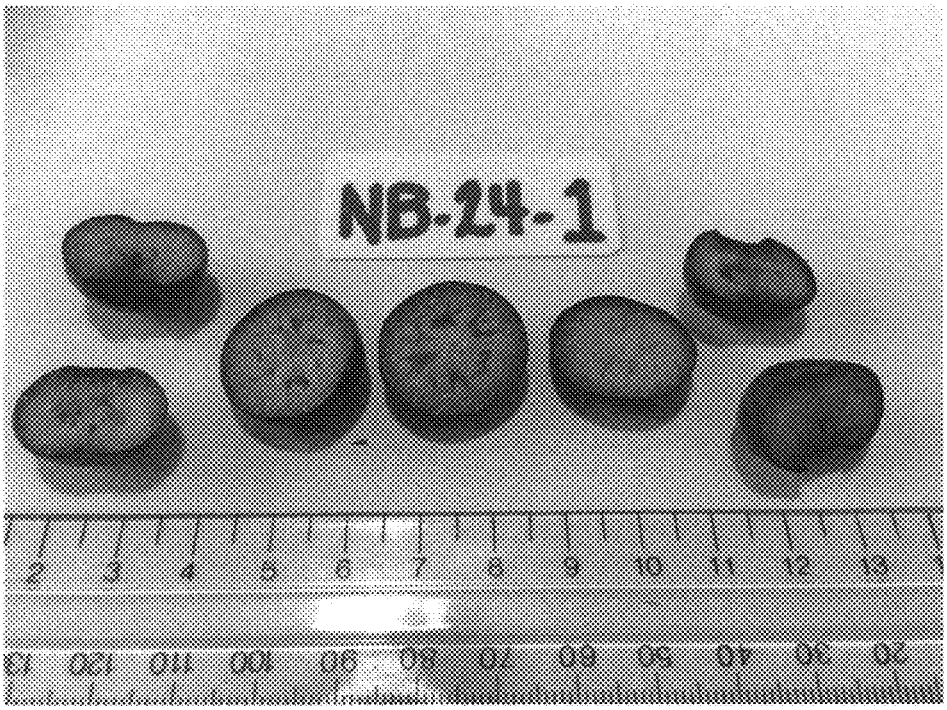
FIG. 2 is are photographs of the new variety 'MG11654-24-001' at approximately 1 year of age, demonstrating the plant's fruit.
Figure 2:
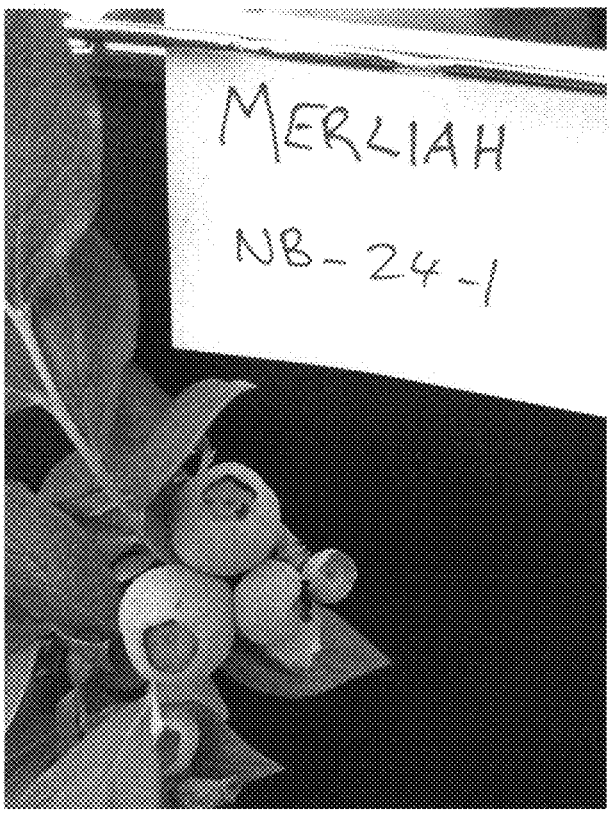
Figure 3:
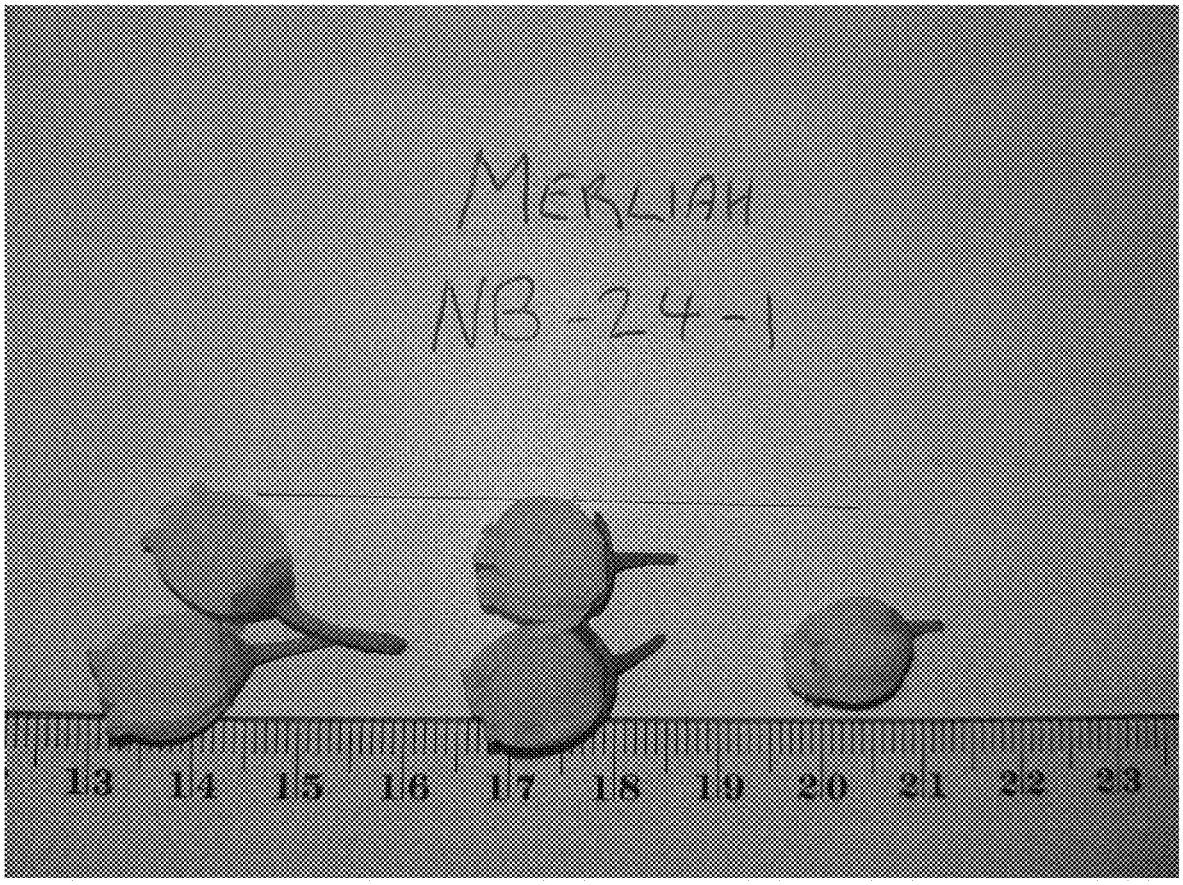
FIG. 3 is a photograph of the new variety 'MG11654-24-001' at approximately 1 year of age, demonstrating the plant's flowers.

The colors in the photographs are as close as possible with the photographic and printing technology utilized. The color values cited in the detailed botanical description accurately describe the colors of the new blueberry.

DETAILED BOTANICAL DESCRIPTION

The following detailed description sets forth the distinctive characteristics of 'MG11654-24-001'. The data which defines these characteristics was collected from asexual reproductions of the original selection. Dimensions, sizes, colors, and other characteristics are approximations and averages set forth as accurately as possible. The plant history was taken on plants approximately 3 years of age, and the descriptions relate to plants grown in the field in Moondarra, Victoria, Australia. Descriptions of fruit characteristics were made on fruit grown in Moondarra, Victoria, Australia. Color designations are from The Royal Horticultural Society Colour Chart (sixth edition).

Classification:
- a. *Family*.—Ericaceae.
- b. *Genus*.—*Vaccinium*.
- c. *Species*.—hybrid.
- d. *Common name*.—Blueberry.

Parentage:
- *Female parent*.—'Duke'. (not patented).
- *Male parent*.—'Ridley 1403'. (U.S. Pat. No. 25,432).

Market class: A fruiting plant intended for the fresh fruit market.

PLANT

General:
- a. *Parentage*.—'Duke' x 'Ridley1403'.
- b. *Plant height*.—1-1.2 m.
- c. *Plant width*.—0.9-1.1 m.
- d. *Growth habit*.—Upright/whippy.
- e. *Growth* (*vigor*).—Moderate to strong.
- f. *Productivity*.—Medium to high (~7.1 kg/bush).
- g. *Cold hardiness*.—Not tested.
- h. *Cold tolerance*.—Not tested.
- i. *Chilling requirement*.—Not tested.
- j. *Tolerance to disease*.—Not tested.
- k. *Leafing*.—Moderate to strong.
- l. *Twigginess*.—Low to moderate.

STEM

General:
- a. *Suckering tendency*.—3-4/plant.
- b. *Mature cane color*.—159CD/197A.
- c. *Mature cane length*.—0.7-0.9 m.
- d. *Mature cane width*.—1-1.3 cm.
- e. *Bark texture*.—Medium roughness.
- f. *Surface texture of new wood*.—Smooth.
- g. *Internode length on strong, new shoots*.—27-31 mm.
- h. *Fruiting wood*.—To 16 cm in length.

FOLIAGE

General:
- a. *Time of beginning of leaf bud burst*.—Mid-late September.
- b. *Leaf color* (*top side*).—133A/135A.
- c. *Leaf color* (under side).—146C.
- d. *Leaf arrangement*.—Alternate.
- e. *Leaf shape*.—Elliptic.
- f. *Leaf margins*.—Entire.
- g. *Undulation of margin*.—Weak.
- h. *Leaf venation*.—Reticulate.
- i. *Leaf apices*.—Acute.
- j. *Leaf bases*.—Obtuse.
- k. *Leaf length*.—55-58 mm.
- l. *Leaf width*.—26-33 mm.
- m. *Leaf length/width ratio*.—Medium; 1:0.47-1:0.56.
- n. *Leaf nectarines*.—Absent.
- o. *Pubescence of upper side*.—Absent.
- p. *Pubescence of lower side*.—Absent.
- q. *Cross sectional profile*.—Flat.
- r. *Longitudinal profile*.—Straight.
- s. *Attitude*.—Semi-upright.

Petioles:
- a. *Length*.—5 mm.
- b. *Width*.—1-2 mm.
- c. *Color*.—Yellow-Green N144D/145A.

FLOWERS

General:
- a. *Time of beginning of flowering*.—Early; September at Moondarra, Victoria, Australia.
- b. *Time of* 50% *anthesis*.—20-28$^{th}$ September.
- c. *Flower shape*.—Urceolate.

d. *Flower bud density*.—moderate.
e. *Flower fragrance*.—Weak; sweet smell.

Corolla:
*Length*.—11-12 mm.
*Width*.—10-12 mm.
*Aperture width*.—5-6 mm.
*Anthocyanin coloration of corolla*.—Absent.
*Corolla ridges*.—Present.
*Protrusion of stigma*.—0-1 mm.

Inflorescence:
a. *Length*.—55-57 mm.
b. *Diameter*.—40-43 mm.
c. *Length of peduncle*.—14-15 mm.
d. *Surface texture of peduncle*.—Smooth.
e. *Color of peduncle*.—Mix N144A/144A.
f. *Length of pedicel*.—5-7 mm.
g. *Surface texture of pedicel*.—Smooth.
h. *Color of pedicel*.—143C/145B.
i. *Number of flowers per cluster*.—6.
j. *Flower cluster density*.—Light to moderate.

Calyx (with sepals):
a. *Diameter*.—7-9 mm.
b. *Color* (*sepals*).—145B.

Stamen:
a. *Length*.—7-8 mm.
b. *Number per flower*.—9-10.
c. *Filament color*.—149C.

Style:
a. *Length*.—9 mm.
b. *Color*.—145B.

Pistil:
a. *Length*.—11-12 mm.
b. *Ovary color* (*exterior*).—144A/137C.

Anther:
a. *Length*.—4 mm.
b. *Number*.—9-10.
c. *Color*.—167A/165B.

Pollen:
a. *Abundance*.—Medium.
b. *Color*.—N/A
c. *Self-compatibility*.—Good (~75%). .

FRUIT

General:
a. *Time of fruit ripening*.—Very early; December in Moondarra, Victoria, Australia.
b. *Time of* 50% *maturity*.—November/December.
c. *Fruit development period*.—Approximately 70 days.
d. *Cluster density*.—Approximately 22 berries per cluster.
e. *Unripe fruit color*.—138D.
f. *Ripe berry color*.—203C/103A.
g. *Berry surface wax abundance*.—Moderate to strong.
h. *Berry flesh color*.—157A/195D.
i. *Berry weight*.—3.3 g.
j. *Berry height from calyx to scar*.—10-11 mm.
k. *Berry diameter*.—19-21 mm.
l. *Berry shape*.—Oblate.
m. *Fruit stem scar*.—Small/dry.
n. *Sweetness when ripe*.—Medium to high.
o. *Firmness when ripe*.—Firm.
p. *Acidity when ripe*.—Medium to high.
q. *Storage quality*.—Good.
r. *Suitability for mechanical harvesting*.—Not suitable.
s. *Self-fruitfulness*.—Yes.
t. *Uses*.—Fresh fruit.
u. *Type*.—on one-year old shoots only.

SEED

General:
a. *Seed abundance in fruit*.—High.
b. *Seed length*.—1-2 mm.

COMPARISON BETWEEN PARENTAL AND COMMERCIAL CULTIVARS

| Organ | Context | 'MG11654-24-001' | 'Ridley 1403' (U.S. Pat. No. 25,432) | 'Brigitta' (not patented) |
|---|---|---|---|---|
| Plant | Vigour | Strong | Strong | Medium |
| Plant | Growth habit | Upright to semi-upright | Upright to semi-upright | Upright |
| One-year-old shoot | Colour | Green | Green | Green |
| One-year-old shoot | Length of internode | Medium; 27-31 mm | Medium | Medium |
| Leaf | Length | Long; 55-58 mm | Long to very long | Long |
| Leaf | Width | Broad; 26-33 mm | Broad | Broad |
| Leaf | Shape | Elliptic | Elliptic | Elliptic |
| Leaf | Colour of upper side | Green; 133A/135A | Green | Green |
| Leaf | Intensity of green colour on upper side (varieties with green leaf colour only) | Medium | Medium | Medium |
| Leaf | Margin | Entire | Entire | Serrate |
| Flower bud | Anthocyanin coloration | Weak | Weak | Medium-strong |
| Flower | Shape of corolla | Urceolate | Urceolate | Urceolate |
| Flower | Size of corolla tube | Medium | Medium to large | Medium |
| Flower | Anthocyanin colouration of corolla tube | Absent or very weak | Absent or very weak | Absent or very weak |
| Flower | Ridges on corolla tube | Present | Present | Present |
| Fruit cluster | Density | Medium to dense | Medium to dense | Medium-dense |
| Unripe fruit | Intensity of green colour | Light to medium | Light | Light |
| Fruit | Size | Large to very large; 19-21 mm | Very large | Medium |
| Fruit | Shape in longitudinal section | Oblate | Round | Oblate |
| Fruit | Attitude of sepals | Erect | Erect | Erect |

-continued

| Organ | Context | 'MG11654-24-001' | 'Ridley 1403' (U.S. Pat. No. 25,432) | 'Brigitta' (not patented) |
|---|---|---|---|---|
| Fruit | Diameter of calyx basin | Large | Large | Small-medium |
| Fruit | Depth of calyx basin | Shallow to medium | Deep | Deep |
| Fruit | Intensity of bloom | Strong | Medium | Medium |
| Fruit | Colour of skin | Dark blue; 203C/103A | Dark blue | Dark blue |
| Fruit | Firmness | Firm | Very firm | Medium |
| Fruit | Sweetness | High | High | Low-medium |
| Fruit | Acidity | Medium to high | Low | Low-medium |
| Time of | Vegetative bud burst | Early | Early | Medium |
| Time of | Beginning | of flowering | Very early | Early Medium |
| Time of | Beginning | of fruit ripening | Very early | Early Medium |

The invention claimed is:

1. A new and distinct variety of blueberry plant named 'MG11654-24-001', substantially as illustrated and described herein.

* * * * *